United States Patent [19]
Wong et al.

[11] Patent Number: 6,071,741
[45] Date of Patent: Jun. 6, 2000

[54] DOC TUMOR SUPPRESSOR PROTEIN AND GENE

[75] Inventors: David T. W. Wong, Newton; Randy Todd, Boston, both of Mass.

[73] Assignee: General Hospital Corporation, Charlestown, Mass.

[21] Appl. No.: 08/728,839

[22] Filed: Oct. 10, 1996

Related U.S. Application Data

[60] Provisional application No. 60/005,115, Oct. 12, 1995.

[51] Int. Cl.[7] ............................. C12N 15/00; C07H 21/04; A61K 38/00
[52] U.S. Cl. ...................... 435/320.1; 536/23.5; 530/324
[58] Field of Search ........................... 536/23.5; 530/324; 435/7.23, 6, 320.1

[56] References Cited

U.S. PATENT DOCUMENTS

| | | | |
|---|---|---|---|
| 5,324,654 | 6/1994 | Bredsen | 435/240.2 |
| 5,386,013 | 1/1995 | Lee et al. | 530/350 |
| 5,426,181 | 6/1995 | Lee et al. | 536/23.5 |

OTHER PUBLICATIONS

Boyd et al. (1988) *J. Oral. Path.* 17:193–201.
Weinberg (1991) *Science* 254:1138–1146.
Moroco et al. (1990) *Lab. Invest.* 63:298–306.
Kim et al. (1993) *Anticancer Res.* 13:1405–1414.
Kimichi et al. (1988) *Science* 240:196.
Ankathil et al. (1994) *J. Oncol. Rep.* 1:1011–1015.
Polverini et al. (1988) *Carcinogenesis* 9:117–122.
Rastinejad et al. (1989) *Cell* 56:345–355.
Vilcek et al. (1986) *J. Exp. Med.* 163:632.
Sugarman et al. (1985) *Science* 220:943.
Lachman et al. (1987) *J. Immunol* 138:2913.
Husain et al. (1989) *Proc. Natl. Acad. Sci.* (USA) 86:1264–1268.
Odukoya et al. (1983) *J. Natl. Can. Inst.* 71:1252–1264.
Polverini et al. (1987) *Lab. Invest.* 54:432–441.
Polverini et al. (1988) *J. Oral Path.* 17:522–527.
Frohman et al. (1988) *Proc. Natl. Acad. Sci.* (USA)85:8998–9002.
Gordon et al. (1992) *J. Immunol.* 148:4021–4027.
Tadokoro et al. (1989) *Oncogene* 4:499–505.
Scully (1992) *British Dental Journal* 173:53–59.
Lehman et al. (1991) *Environmental Health Perspectives* 93:133–144.
Issing et al. (1993) *Anticancer Research* 13:2541–2552.
Bouk et al. (1986) *Cancer Research* 46:5101–5105.
Brennan et al. (1995) *The New England Jounal of Medicine* 332:429–435.
Field (1992) *Eur. J. Cancer Vol.* 28B : 67–76.
Kopf et al. (1993) *Nature (Lond)* 326:245–247.
Todd et al. "Deleted in oral cancer–1 (doc–1), a novel oral tumor suppressor gene" FASEB J. vol. 9, pp. 1362–1370, 1995.
Tsuji et al. "Molecular cloning and TNF–a Mediated expression of the human doc–1 oral tumor suppressor gene" Proceedings of the American Association for Cancer Research. vol. 37 p. 591, 1996.

*Primary Examiner*—Yvonne Eyler
*Attorney, Agent, or Firm*—Hale and Dorr LLP

[57] ABSTRACT

Disclosed is an isolated tumor suppressor protein inducible by tumor necrosis factor. Also disclosed are isolated cDNA molecules encoding the doc-1, a tumor suppressor protein, cells transformed with this cDNA, antibodies specific for and reactive with the doc-1 protein, and methods of using these proteins, cDNAs, and antibodies.

6 Claims, 11 Drawing Sheets

| FIG. 3A-1 |
|---|
| FIG. 3A-2 |
| FIG. 3A-3 |
| FIG. 3A-4 |

FIG. 3A

Sequence Range: 1 to 1023

```
             10         20         30         40         50         60         70         80
              *          *          *          *          *          *          *          *
    CCCGCGGGGA TGTCGTACAA GCCGAACTTG ACCGGCACA TGCCCCGCCGC CGCCCTCAAC GCCGGAAGTG TCCACTCACC 90        100        110        120        130        140
              *          *          *          *          *          *
    ATCTACTAGC ATG GCG ACA TCC TCC CAA TAT CGC CAG CTG CTG AGT GAC TAC GGA CCA CCG TCA CTA
               Met Ala Thr Ser Ser Gln Tyr Arg Gln Leu Leu Ser Asp Tyr Gly Pro Pro Ser Leu
        <_a__a__a__a__a_TRANSLATION OF DOC-1 [A]_a__a__a__a__a__a__a_>
```

FIG. 3A-1

```
150         160         170         180         190         200         210
 *           *           *           *           *           *           *
GGC TAC ACC CAG GGA ACT GGA AAT AGC CAA GTG CCT CAG AGT AAA TAT GCA GAA CTG CTG GCC ATC
Gly Tyr Thr Gln Gly Thr Gly Asn Ser Gln Val Pro Gln Ser Lys Tyr Ala Glu Leu Leu Ala Ile>
 a   a   a   a   a   a   a   a   a   a   a__TRANSLATION OF DOC-1 [A]__a   a   a   a   a   a   a 220         230         240         250         260         270
 *           *           *           *           *           *
ATT GAA GAG TTG GGG AAA GAG ATC AGA CCC ACT TAT GCG GGA AGC AAG AGC GCC ATG GAA AGA CTA
Ile Glu Glu Leu Gly Lys Glu Ile Arg Pro Thr Tyr Ala Gly Ser Lys Ser Ala Met Glu Arg Leu>
 a   a   a   a   a   a   a   a   a   a   a__TRANSLATION OF DOC-1 [A]__a   a   a   a   a   a   a 280         290         300         310         320         330         340
 *           *           *           *           *           *           *
AAA CGA GGC ATC ATT CAT GCC CGA AGC CTG GTT CGG GAG TGC TTG GCT GAA ACG GAA CGT AAT GCC
Lys Arg Gly Ile Ile His Ala Arg Ser Leu Val Arg Glu Cys Leu Ala Glu Thr Glu Arg Asn Ala>
 a   a   a   a   a   a   a   a   a   a   a__TRANSLATION OF DOC-1 [A]__a   a   a   a   a   a   a
```

FIG. 3A-2

```
        350        360        370        380        390        400        410        420
         *          *          *          *          *          *          *          *
AGG TCC TAGCCCCTG GCCAGTCTGA AGGCCCATCT TGCTACCCCT TGGAGATGAG AGGCTTTGTT CAAAATGGCA
Arg Ser>
  a   >

430        440        450        460        470        480        490        500
    *          *          *          *          *          *          *          *
GTTTCCTGC CATGGTCATT AAGCTCTGAA CCCACATTCA AAAGACTGAG AAGACATTTT GCAGTTACTG ATGATGTGCA 510        520        530        540        550        560        570        580
    *          *          *          *          *          *          *          *
TTTAAGTAG TTAGGAACAA TCCAAGCATT GATTTTAAAG ATGTTTGTGA AGCCACTTCA CAGCAAGCTA TTGTTTTCCC 590        600        610        620        630        640        650        660
    *          *          *          *          *          *          *          *
CCAAATACCA GTGTCCCCTT AATCTCCCTT TGGATACATT TGCCATTGC ATCACCCCAG TTGACTTCCT TTCCAGGAGG
```

FIG. 3A-3

```
       670        680        690        700        710        720        730        740
        *          *          *          *          *          *          *          *
TCACCTGCCT CTGAGGACCT GAGTGCAAAC CACAGCACGT TTGTTTAGTA GCTGGCCCGC CTGTGTACAC CCTGCTTCAC 750        760        770        780        790        800        810        820
        *          *          *          *          *          *          *          *
GGAGCTTCTC TGCTTAAGTG TTTGCATGAC TGAGTGCTTT GAAGTCAATC TTAAAAATGC ACAAGTTACA GATACAGAAG 830        840        850        860        870        880        890        900
        *          *          *          *          *          *          *          *
AAGAGGCGATC TCCAACCTAC CAAGCGCCCT GCAAATGTCC ATCCTGAGAC TGTAGTTCTC GGTTCCATGT TTACTGTGAG 910        920        930        940        950        960        970        980
        *          *          *          *          *          *          *          *
ATGATCACAA CATCTGGAAG AAAATGACTG AAACTGTTGC ATCTTTGTAT TTATTACTTG ATGTAATAAA GCTTATTTC 990       1000       1010       1020
        *          *          *          *
ATTAACAGTT TGTATTAAGA AAAAAAAAAA AAAAAAAAA AAA
```

FIG. 3A-4

Sequence Range 1 to 63

```
         10           20           30           40           50           60
*         *            *            *            *            *            *
ATC ATT CAT CCC CCA ACC CTC CTT CCC CAC TCC TTC CCT CAA ACC CAA CCC AAC CCC ACC
Ile Ile His Ala Arg Ser Leu Val Arg Glu Cys Leu Ala Glu Thr Glu Arg Asn Ala Arg
 a   a   a   a   a   a   a   a   a   a   a   a   a   a  [A]  a   a   a   a   a
          TRANSLATION OF PLACENTA CODING REGION
```

FIG. 3B

DOC TUMOR SUPPRESSOR PROTEIN AND GENE

CROSS-REFERENCE TO RELATED APPLICATIONS

This application claims priority to Provisional Patent Application Ser. No. 60/005,115 entitled "A NOVEL TUMOR SUPPRESSOR PROTEIN AND GENE", filed Oct. 12, 1995.

FUNDING

This invention was made with Government support under Grant nos. DE-10208 and DE-08680, awarded by the National Institutes of Health, and as such the Government has certain rights in the invention.

FIELD OF THE INVENTION

This invention relates to a novel tumor repressor protein, doc-1, inducible by tumor necrosis factor, and to nucleic acid encoding doc-1. This invention also relates to the treatment of carcinoma by inducing the expression of tumor repressor genes in carcinoma tissues.

BACKGROUND OF THE INVENTION

Carcinoma of the oral cavity, which is the sixth most common cancer in the world, accounts for about four percent of all cancers and about two percent of all cancer deaths (reviewed in Ankathil et al. (1994) Oncol. Rep. 1:1011–1015). Oral squamous cell carcinoma in particular is newly diagnosed in 50,000 Americans and in 500,000 others worldwide each year (Vokes et al. (1993) N. Engl. J. Med. 328:184–94). Approximately half of the patients afflicted will die within five years of diagnosis while surviving patients may be left with severe esthetic and/or functional compromise (Silverman et al. (1990) J. Am Dent. Assoc. 120:495–499).

Squamous cell oral cancer is usually treated with surgery, radiation therapy, or combined modality therapy. Such treatments, however, may cause non-trivial complications such as xerostomia, poor wound healing, major vessel erosion, and increased risk for the delayed development of secondary neoplasms. (Lebovics in Harrison's Principles of Internal Medicine, 13 th Ed. (Isselbacher et al., eds) McGraw-Hill, Inc., New York) pp. 1850–1853). Furthermore, radical surgery may severely compromise both the appearance and functional and communicative abilities of the patient. Chemotherapy is not used as an initial treatment, and its role as an adjunct therapy is disputed (Lebovics, ibid). Thus, better therapeutic methods for treating oral carcinoma in humans are greatly needed.

Several etiological agents are suspected of causing oral cancer. Predisposing factors such as tobacco use and alcohol consumption have been identified, but there are oral cancer patients who have neither smoked not drunk alcohol for whom the cause cannot be established. Some metabolic deficiencies have been incriminated in oral cancer development, but the mechanisms have not been elucidated. Viral associations have been demonstrated, but whether the virus is an etiological agent has yet to be determined.

The majority of human cancers (70–90%), and oral carcinomas in particular, are thought to be caused by chemically-induced mutagenesis from the environment, either directly or indirectly (Boyd et al. (1988) J. Oral. Path. 17:193–201). These mutagens produce point mutations, deletions, insertions or rearrangements which may activate or suppress genes responsible for tumor phenotypes (Boyd et al. (1988) J. Oral. Path. 17:193–201; and Weinberg (1991) Science 254:1138–46). The activation of specific oncogenes including c-erb, DCC, Bi, Ki-ras, Ha-ras, and c-myc has also been demonstrated in oral tumors.

The loss of function of another group of genes, the tumor suppressor genes, is also implicated in carcinogenesis. Active suppressor genes in normal cells are thought to function as negative regulators of a number of growth processes, including recognition and response to growth and differentiation signals, overriding the transforming effects of oncogenes, immunity to tumors, and inhibition of angiogenic activity (see, Moroco et al. (1990) Lab. Invest. 63:298–306).

In the case of head and neck cancers, the role of at least four tumor suppressor genes has been suggested. For example, certain human oral cancer cell lines were found not to contain "deleted in colon cancer" (DCC) mRNAs (Kim et al (1993) Anticancer Res. 13:1405–1414). Some cells lacking the retinoblastoma (RB) tumor suppressor gene were found to lack receptors to, and sensitivity for, TGF-β-mediated differentiation (Kimichi et al. (1988) Science 240:196). Overexpression of a mutant form of p53 tumor suppressor protein encoded by the p53 oncogene, and lack of expression of wild type p53 protein was detected, while down-regulation of E-cadherin was found to be associated with both invasion and metastasis (reviewed in Ankathil et al. (1994) J. Oncol. Rep. 1:1011–1015). Furthermore, somatic cell hybridization studies using oral keratinocytes isolated from the cheek pouch of a hamster model of human oral cancer have also suggested the presence of tumor suppressor genes (see, e.g., Polverini et al. (1988) Carcinogenesis 9:117–22; Rastinejad et al. (1989) Cell 56:345–55; Moroco et al. (1990) Lab. Invest. 63:298–306). It has recently shown, using normal malignant hamster oral keratinocyte hybrids from this model, that acquisition of three transformed phenotypes (angiogenesis, immortality, and anchorage independence) is linked to the loss of several suppressor gene functions (Moroco et al. (1990) Lab. Invest. 63:298–306). These malignant phenotypes can be suppressed using somatic cell hybridization analysis, further linking the loss of suppressor genes to the onset of various transformed phenotypes (see, e.g., Polverini et al. (1988) Carcinogenesis 9:117–22; Rastinejad et al. (1989) Cell 56:345–55; Moroco et al. (1990) Lab. Invest. 63:298–306).

SUMMARY OF THE INVENTION

A novel tumor suppressor gene, doc-1, has been discovered which is structurally altered during oral carcinogenesis and which is expressed by normal and not transformed hamster oral keratinocytes and human tissues, and not by oral carcinoma. It has also been discovered that the expression of this gene as a tumor suppressor protein is inducible in cells with tumor necrosis factor (TNF).

These discoveries have been exploited to provide the present invention which, in a first aspect, provides an isolated tumor repressor protein inducible by a TNF. In some embodiments, this tumor repressor protein, doc-1, includes 89 amino acids and has the sequence set forth as SEQ ID NO:1. In other embodiments, the doc-1 protein contains the amino acid sequence set forth as SEQ ID NO:2.

Another aspect of the invention is an isolated cDNA molecule encoding the doc-1 tumor suppressor protein. In preferred embodiments, this cDNA includes the nucleotide sequence set forth as SEQ ID NO:3 or as SEQ ID NO:4.

A cell transformed with one of the isolated cDNAs encoding the doc-1 protein as described above is yet another aspect of the invention. In some embodiments, this cell is a carcinoma cell such as an oral squamous carcinoma cell.

Yet another aspect of the present invention is a method of screening for an oral carcinoma cell. In this method, in situ hybridization is performed on a cell sample using a cDNA encoding the doc-1 tumor suppressor protein. In some embodiments, this cDNA includes the nucleotide sequence set forth as SEQ ID NO:3. In other embodiments, this cDNA includes the nucleotide sequence set forth as SEQ ID NO:4. If the sample is an oral carcinoma cell, the cDNA will not hybridize to the sample.

Another method of screening for an oral carcinoma cell is provided by the invention. In this method a cell sample is treated with an antibody specific for and reactive with the doc-1 tumor suppressor protein, the antibody not reacting with the sample if the sample is an oral carcinoma cell.

In another aspect, a method of inducing the expression of a tumor suppressor protein is provided which comprising the step of treating the cell with a tumor necrosis factor. In one embodiment, the tumor necrosis factor is tumor necrosis factor-alpha.

In another aspect, the invention provides a method of suppressing proliferation of a carcinoma cell in vitro comprising the step of transforming the carcinoma cell with nucleic acid encoding the doc-1 tumor suppressor gene. In one embodiment, the method includes the additional step of administering tumor necrosis factor alpha to the transformed cell. The cell, in some embodiments is an oral carcinoma cell.

In yet another aspect, the invention provides a method of treating a carcinoma in a subject comprising the step of administering a therapeutic amount of tumor necrosis factor alpha to the site of the carcinoma. In some embodiments the carcinoma is an oral carcinoma such as an oral squamous cell carcinoma. The method may further comprise the step of administering to the carcinoma a nucleic acid encoding the doc-1 tumor suppressor gene before administering the tumor necrosis factor to the site.

An alternative method of treating a carcinoma in a subject comprising the step of administering to the carcinoma a nucleic acid encoding the doc-1 tumor suppressor gene. In some embodiments, this step is followed by administering a therapeutic amount of tumor necrosis factor alpha to the site of the carcinoma.

An antibody specific for and reactive with the doc-1 tumor suppressor protein is also provided by the invention.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 3A is a schematic representation of the nucleotide and predicted amino acid sequences of hamster doc-1, wherein the predicted translation starts at nucleotide 91 and ends at nucleotide 351;

FIG. 3B is a schematic representation of the nucleotide and predicted amino acid sequences of human doc-1;

DETAILED DESCRIPTION OF THE PREFERRED EMBODIMENTS

Figure 1A:
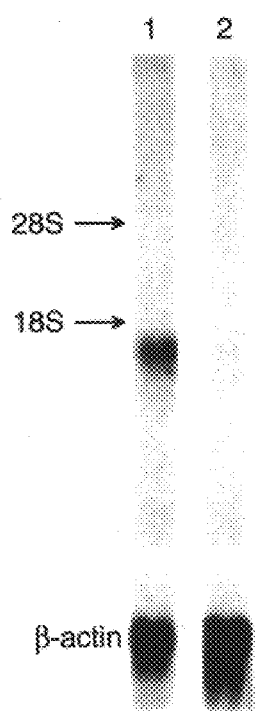
FIG. 1A is a Northern blot showing the presence and absence of doc-1 mRNA in normal (Type I (lane 1)) and malignant (HCPC-1 (lane 2)) hamster oral keratinocytes, respectively.

The patent and scientific literature referred to herein establishes the knowledge that is available to those with skill in the art. The issued U.S. patents, allowed applications, published foreign applications, and references cited herein are hereby incorporated by reference.

The present invention provides a tumor suppressor protein which is inducible with tumor necrosis factor (TNF). As used herein, the term "tumor suppressor protein" refers to a protein which indirectly or directly acts to inhibit tumor cell growth. "Inducible with TNF" refers to the ability of TNF to directly or indirectly initiated the transcription and translation of the tumor suppressor protein.

In particular, the present invention provides in substantially pure form isolated doc-1 tumor suppressor protein, nucleic acid encoding the doc-1 tumor suppressor protein, peptide fragments of the protein, functional derivatives of the nucleic acid and protein, antibodies specific for and reactive with the doc-1 tumor suppressor protein, fragments of such antibodies, and methods of using these molecules in diagnosis, therapy, and study of cancer.

By "substantially pure" is meant any protein or peptide of the present invention, or any cDNA sequence encoding any such protein or peptide, which is essentially free of other proteins or DNA sequences, respectively, or of other contaminants with which it might normally be found in nature, and, as such, exists in a form not found in nature.

The invention provides nucleic acid, and more specifically, cDNA which encodes the doc-1 protein. By "cDNA" is meant complementary or copy DNA produced from an RNA template by the action of RNA-dependent DNA polymerase (reverse transcriptase). Thus, a "cDNA clone" means a duplex DNA sequence complementary to an RNA molecule of interest, carried in a cloning vector. In hamsters, the cDNA of the invention may include a nucleic acid sequence set forth in the Sequence Listing as SEQ ID NO:1. In humans, the cDNA of the invention includes the nucleic acid sequence set forth in the Sequence Listing as SEQ ID NO:2. The invention also includes variants of these sequences which encompass the minor sequence changes that do not alter the reading frame nor encode a protein having substantially different physical, and biochemical characteristics as the doc-1 tumor suppressor protein. cDNA molecules of the invention are useful, for example, in synthesizing the doc-1 protein and in diagnostic methods for identifying cancerous and noncancerous phenotypes as described below.

One tumor suppressor protein of the invention is doc-1, which in hamsters, contains 89 amino acids set forth in the Sequence Listing as SEQ ID NO:1. In humans, the doc-1 protein contains at least the partial amino acid sequence set forth in the Sequence Listing as SEQ ID NO:2.

It will be understood that the doc-1 protein of the present invention can be purified biochemically or physicochemically from a variety of noncancerous native cell or tissue culture sources. For example, cultured mammalian oral keratinocytes or murine fibroblasts can be used for preparation of naturally occurring doc-1 protein. Alternatively, methods are well known for the synthesis of polypeptides of predetermined sequence on solid phase supports and their subsequent separation from the support.

The invention also provides a recombinant doc-1 protein. Because the doc-1 gene can be isolated or synthesized, the doc-1 polypeptide, or a functional derivative thereof, can be synthesized substantially free of other proteins of mammalian origin in a non-mammalian or mammalian eucaryotic organism.

Also included with the scope of the present invention are all active forms of doc-1 derived from the doc-1 cDNA or transcript, all functional derivatives of the doc-1 protein, and all muteins with doc-1 activity. By "functional derivative" is meant a "fragment", "variant", "analog", or "chemical derivative" of the doc-1 tumor suppressor protein. A functional derivative retains at least a portion of the function of the doc-1 protein which permits its utility in accordance with the present invention. A "fragment" of the doc-1 protein is any subset of the molecule, that is, a shorter peptide. A "variant" of the doc-1 protein refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444). Standard reference works setting forth the general principles of recombinant DNA technology including cloning techniques include Watson et al. (*Molecular Biology of the Gene*, Vols. I and II, The Benjamin/Cummings Publishing Co., Inc., Menlo Park, Calif. (1987); Darnell et al., *Molecular Cell Biology*, Scientific American Books, Inc., NY, N.Y. (1986); Lewin *Genes II*, John Wiley & Sons, NY, N.Y. (1985); Old et al., *Principles of Gene Manipulation: An Introduction to Genetic Engineering*, 2d ed., Univ. of California Press, Berkeley, Calif. (1981); and Sambrook et al., *Molecular Cloning: A Laboratory Manual*, Cold Spring Harbor Laboratory Press, Cold Spring Harbor, N.Y. (1989)).

Oligonucleotides representing a portion of the doc-1 nucleic acid sequence are useful for screening for the presence of homologous genes and for the cloning of such genes. Techniques for synthesizing such oligonucleotides are disclosed, e.g., by Wu et al. (*Prog. Nuc. Acid. Res. Molec. Biol.* (1978) 21:101–141). Because the genetic code is degenerate, more than one codon may be used to encode a particular amino acid (Watson in *Molecular Biology of the Gene*, 4th Ed., Benjamin/Cummings Publishing Co., Inc., Menlo Park, Calif. (1987)). Thus, using the genetic code, one or more different oligonucleotides can be identified, each of which would be capable of encoding the amino acid. The oligonucleotide, or set of oligonucleotides, containing the theoretical "most probable" sequence capable of encoding the doc-1 fragment is used to identify the sequence of a complementary oligonucleotide or set of oligonucleotides which is capable of hybridizing to the most probable sequence, or set of sequences. An oligonucleotide containing such a complementary sequence can be employed as a probe to identify and isolate the doc-1 gene (Sambrook et al., supra) A suitable oligonucleotide, or set of oligonucleotides, which is capable of encoding a fragment of the doc-1 gene, e.g., having SEQ ID NO:3, 4, or portions thereof, (or which is complementary to such an oligonucleotide, or set of oligonucleotides) is identified (using the above-described procedure), synthesized, and hybridized by means well known in the art, against a DNA, or more preferably, a cDNA preparation derived from cells which are capable of expressing the doc-1 gene, such as normal oral keratinocytes. Single stranded oligonucleotide molecules complementary to the most probable doc-1 protein coding sequences can be synthesized using procedures which are well known to those of ordinary skill in the art (see. e.g., Belagaje et al. (1979) *J. Biol. Chem.* 254:5765–5780; Maniatis et al. in *Molecular Mechanisms in the Control of Gene Expression*, (Nierlich et al., eds.), Acad. Press, NY (1976)). Additionally, DNA synthesis may be achieved through the use of automated synthesizers. Techniques of nucleic acid hybridization are disclosed by Sambrook et al. (supra), and by Haymes et al. (In: *Nucleic Acid Hybridization, A Practical Approach*, IRL Press, Washington, D.C. (1985)).

In an alternative way of cloning the doc-1 gene, a library of expression vectors is prepared by cloning DNA or, more preferably, cDNA (from a cell capable of expressing doc-1 into an expression vector. By "cDNA library" is meant a collection of recombinant DNA molecules containing cDNA inserts which together comprise the entire expressible genome of an organism. Such a cDNA library may be prepared by methods known to those of skill, and described, for example, in Sambrook et al. (supra) . Generally, RNA is first isolated from the cells of an organism from whose genome it is desired to clone a particular gene. Preferred for the purposes of the present invention are mammalian, most preferably, human, cell lines. The library is then screened for members capable of expressing a protein which binds to anti-doc-1 antibody, and which has a nucleotide sequence that is capable of encoding polypeptides that have the same amino acid sequence as doc-1 proteins or peptides, or fragments thereof. The DNA, or more preferably cDNA, is extracted and purified from a cell which is capable of expressing doc-1 protein. The purified cDNA is fragmentized (by shearing, endonuclease digestion, etc.) to produce a pool of DNA or cDNA fragments. DNA or cDNA fragments from this pool are then cloned into an expression vector in order to produced a genomic library of expression vectors whose members each contain a unique cloned DNA or cDNA fragment.

A DNA sequence encoding the doc-1 protein of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., (supra), and are well known in the art.

The present invention encompasses the expression of the doc-1 protein (or a functional derivative thereof) in either prokaryotic or eucaryotic cells, although eucaryotic expression is preferred. Preferred eucaryotic hosts including yeast, insects, fungi, and mammalian cells either invivo, or in tissue culture. Mammalian cells provide posttransitional modifications to protein molecules including correct folding or glycosylation at correct sites. For a mammalian cell host, many possible vector systems are available for the expression of the doc-1 gene. A wide variety of transcriptional and translations regulatory sequences may be employed, depending upon the nature of the host. The transcriptional and translational regulatory signals may be derived from viral sources, such as adenovirus, bovine papilloma virus, Simian virus 40, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Of interest are regulatory signals which are temperature-sensitive so that by varying the temperature, expression can be repressed or initiated, or are subject to chemical regulation, e.g., metabolite.

The present invention also provides a method of treating a cancerous cell or of inhibiting the proliferation of a carcinoma cell with gene therapy using a cDNA or other nucleic acid encoding doc-1 to transform the cell. Any type of carcinoma can be treated with the method of the invention, including squamous cell oral carcinoma, promyelocytic leukemia HL-60, HeLa cell S3, chronic myelogenous leukemia K-562, lymphoblastic leukemia MOLT-4, Burkitt's lymphoma Raji, colorectal adenocarcinoma SW480, lung carcinoma A549, and melanoma G361.

To transform a carcinoma cell or any cell in which doc-1 expression is desired, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototropy to an auxotrophic host, biocide resistance, e.g., antibiotics, or heavy metals, such as copper or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama (*Mol. Cell. Biol.* (1983) 3:28).

Genetic constructs encoding doc-1 functional derivatives thereof such as those described above, can be used in gene therapy. An abnormal doc-1 molecule which results in enhanced susceptibility to cancer, may be replaced by infusion of cells of the desired lineage (such as keratinocytes, for example) transfected with DNA encoding normal or modified doc-1 protein, under conditions where the infused cells with preferentially replace the endogenous cell population. Thus, the invention provides a method of inhibiting the proliferation of cancer cells in vivo or in vitro.

The method also includes inducing the expression of the doc-1 gene by the administration of, or treatment with, TNF or a biologically active fragments thereof.

TNF is a regulatory cytokine produced by activated monocytes and macrophages, among other cells, which has pleiotropic activities, such as the inhibition of cell growth (Vilcek et al. (1986) *J. Exp. Med.* 163:632; Sugarman et al. (1985) *Science* 230:943; Lachman et al. (1987) *J. Immunol.* 138:2913), and cytolysis. Some of the activities of TNF are mediated by the activation of specific genes in the cells upon which it acts. For example, TNF induces connective tissue cell protein TSG-6 (U.S. Pat. No. 5,386,013) and TSG-14 (U.S. Pat. No. 5,426,181). These are different forms of TNF (i.e., TNF-α, TNF-β), either of which are useful in the method of the invention. Preferably, TNF-α is use in the methods of the invention. Oral tumor cells as well as other carcinoma cells do not express doc-1, either because of some event upstream and prerequisite for the transcription and/or translation of the doc-1 gene, or because of the presence of a mutation in the doc-1 gene. If the former is the cause, treatment of the cell with TNF should result in doc-1 expression, and hence a reduction in the cancerous phenotype, including cell proliferation. TNF can be isolated from a tissue source, produced recombinantly, or obtained commercially, for example, from Genzyme (Boston, Mass.).

According to the invention, TNF, or active fragments thereof are administered by any means that achieve induction of doc-1 to treat malignant tumors. For example, administration may be by various parenteral routes such as subcutaneous, intravenous, intradermal, intramuscular, intraperitoneal, intranasal, transdermal, or buccal routes. Alternatively, or concurrently, administration may be by the topical route or the oral route. Parenteral administration can be by bolus injection or by gradual perfusion over time. A typical regimen for preventing, suppressing, or treating a malignant tumor comprises administration of an effective amount of TNF, or the functional derivative thereof over a period of one or several days, up to and including between one week and about six months. It is understood that the dosage administered will be dependent upon the age, sex, health, and weight of the recipient, kind of concurrent treatment, if any, frequency of treatment, and the nature of the effect desired. The ranges of effective doses provided below are not intended to be limiting and represent preferred dose ranges. However, the most preferred dosage will be tailored to the individual subject, as is understood and determinable by one of skill in the art. The total dose required for each treatment may be administered by multiple doses or in a single dose. The protein, functional derivative thereof or antibody may be administered alone or in conjunction with other therapeutics directed to the viral infection, or directed to other symptoms of the viral disease. Effective amounts of TNF, or functional derivative thereof are from about 0.01 $\mu$g to about 100 mg/kg body weight, and preferably from about 10 $\mu$g to about 50 mg/kg body weight, and in culture preferably from about 0.01 $\mu$g/ml to 0.05 $\mu$g/ml.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods. Pharmaceutical compositions comprising TNF as used in the method of the invention include all compositions wherein the protein or fragment is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically. Additional cancer therapeutic drugs may also be included in the therapeutic formulation.

Pharmaceutical compositions include suitable solutions for administration by injection or orally, and contain from about 0.01 to 99 percent, preferably from about 20 to 75 percent of active component (i.e., TNF) together with the excipient. Pharmaceutical compositions for oral administration include tablets and capsules. Compositions which can be administered rectally include suppositories.

Of course, if a mutation in the doc-1 gene is at least partially responsible for the malignant phenotype, gene therapy or transformation with a wild-type doc-1 gene as described above, followed by TNF administration are useful treatment.

The invention also provides antibodies specific for, and reactive with, the doc-1 tumor suppressor protein. Such antibodies are used in methods to detect the presence of, or measure the quantity or concentration of, doc-1 protein in a cell, tissue extract, biological fluid, or other solution. The antibodies may be used in methods for measuring induction of expression of doc-1 in a cell or in methods for identifying a compound capable of inducing the expression of doc-1 in a cell. Antibodies of the invention may also be used to disrupt the activity of doc-1, thereby preventing or treating any disease associated with overproduction, or inappropriate production or action of doc-1.

The term "antibody" is meant to include polyclonal antibodies, monoclonal antibodies, chimeric antibodies, and anti-idiotypic (anti-Id) antibodies. An antibody is said to be "capable of reacting with" a molecule if it is capable of specifically binding with the molecule. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics. An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

In order to predict antigenic epitopes present in the doc-1 protein or fragments thereof, the amino acid sequence of doc-1 is inspected visually or analyzed by computer, for example, using the program of PEPTIDESTRUCTURE, (Jameson et al. (1988) CABIOS 4:181–186). This program allows determination of hydropathicity values which are then used to determine which peptide sequences within the overall protein sequence are likely to be most immunogenic based on their potential secondary structure. Such peptides may be synthesized chemically, or alternatively, and preferably, by recombinant DNA methods.

An alternative method of generating doc-1 is to use a non-synthetic molecule as the antigen. For example, doc-1 protein may be prepared as a bacterially or other cell expressed fusion protein by using an appropriate expression plasmid. The purified fusion protein is employed for the immunization of rabbits to obtain polyclonal antibodies. Polyclonal antibodies are heterogenous populations of antibody molecules derived from the sera of animals immunized with an antigen.

Alternatively, such a fusion protein, or a synthetic peptide ma be used to immunize a rodent for generation of a monoclonal antibody. Monoclonal antibodies are a substantially homogenous population of antibodies to specific antigens. Monoclonal antibodies may be obtained may be obtained by methods known to those skilled in the art (see, e.g., Kohler et al. (1975) Nature 256:495–497 and U.S. Pat. No. 4,376,110). Such antibodies may be of any immunoglobulin class including IgG, IgM, IgE, IgA, and any subclass thereof. The hybridoma producing the monoclonal antibodies of this invention may be cultivated in vitro or in vivo. Production of high titers of monoclonal antibodies in vivo production makes this the presently preferred method of production. Briefly, cells from the individual hybridomas are injected intraperitoneally into pristane-primed BALB/c mice to produce ascites fluid containing high concentrations of the desired monoclonal antibodies. Monoclonal antibodies of isotype IgM or IgG may be purified from such ascites fluids, or from culture supernatants, using column chromatography methods well known to those of skill in the art.

Chimeric antibodies are molecules different portions of which are derived from different animal species, such as those having a variable region derived from a murine monoclonal antibody and a human immunoglobulin constant region. Chimeric antibodies and methods for their production are known in the art (Cabilly et al. (1984) *Proc. Natl. Acad. Sci. (USA)* 81:3273–3277; Morrison et al. (1984) *Proc. Natl. Acad. Sci. (USA)* 81:6851–6855; Boulianne et al. (1984) *Nature* 312:643–646; Neuberger et al. (1985) *Nature* 314:268–270; Taniguchi et al., European Patent Application No. 171496 (published Feb. 19, 1985); Kudo et al., European Patent Application No. 184187 (published Jun. 11, 1986); Robinson et al., International Patent Publication No. PCT/US86/02269 (published May 7, 1987); Sun et al. (1987) *Proc. Natl. Acad. Sci. (USA)* 84:214–218; Better et al. (1988) *Science* 240:1041–1043).

The term "antibody" is also meant to include both intact molecules as well as fragments thereof, such as, for example, Fab and F(ab')$_{21}$ which are capable of binding antigen. Fab and F(ab')$_2$ fragments lack the Fc fragment of intact antibody, clear more rapidly from the circulation, and may have less non-specific tissue binding than an intact antibody (Wahl et al. (1983) *J. Nucl. Med.* 24:316–325). It will be appreciated that Fab and F(ab')$_2$ and other fragments of the antibodies useful in the present invention may be used for the detection and quantitation of doc-1 protein according to the methods disclosed herein for intact antibody molecules. Such fragments are typically produced by proteolytic cleavage, using enzymes such as papain (to produce Fab fragments) or pepsin (to produce F(ab')$_2$ fragments).

The antibodies, or fragments of antibodies, of the present invention may be used to quantitatively or qualitatively detect the presence of cells which express the doc-1 protein on their surface or intracellularly. This can be accomplished by immunofluorescence techniques employing a fluorescently labelled antibody (see below) coupled with light microscopic, flow cytometric, or fluorimetric detection.

The antibodies of the present invention may be employed histologically, as in immunofluorescence or immunoelectron microscopy, for in situ detection of doc-1 protein. In situ detection may be accomplished by removing a histological (cell or tissue) specimen from a subject and providing the a labelled antibody of the present invention to such a specimen. The antibody (or fragment) is preferably provided by applying or by overlaying on the biological sample. Through the use of such a procedure, it is possible to determine not only the presence of the doc-1 protein but also its distribution on the examined tissue. Using the present invention, those of ordinary skill will readily perceive that any of a wide variety of histological methods (such as staining procedures) can be modified in order to achieve such in situ detection.

Additionally, the antibody of the present invention can be used to detect the presence of soluble doc-1 molecules in a biological sample. Used in this manner, the antibody can serve as a means to monitor the presence and quantity of doc-1 proteins in a subject having a condition associated with TNF induction of doc-1, or the lack thereof. Such immunoassays for the doc-1 protein typically comprise incubating a biological sample, such as biological fluid, a tissue extract, freshly harvested cells such as keratinocytes, or cells which have been incubated in tissue culture, in the presence of a detectably labelled antibody capable of identifying the doc-1 protein, and detecting the antibody by any of a number of techniques well-known in the art. The biological sample may be treated with a solid phase support or carrier (which terms are used interchangeably herein) such as nitrocellulose, or other solid support, which is capable of immobilizing cells, cell particles or soluble proteins. The support may then be washed with suitable buffers followed by treatment with the detectably labelled doc-1-specific antibody. The solid phase support may then be washed with the buffer a second time to remove unbound antibody. The amount of bound label on said solid support may then be detected by conventional means. By "solid phase support or carrier" is intended any support capable of binding antigen or antibodies. Well-known supports, or carriers, include glass, polystyrene, polypropylene, polyethylene, dextran, nylon, amylases, natural and modified celluloses, polyacrylamides, gabros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

Detection may be accomplished using any of a variety of other immunoassays. For example, by radioactively labelling the antibodies or antibody fragments, it is possible to detect doc-1 protein through the use of a radioimmunoassay (RIA) (Chard, in: Work et al., *Laboratory Techniques in Biochemistry in Molecular Biology*, North Holland Publishing Company, New York (1978)). The radioactive isotope can be detected by such means as the use of a gamma counter or a liquid scintillation counter or by autoradiography. It is also possible to label the antibody with a fluorescent compound. When the fluorescently labelled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, ophthaldehyde and fluorescamine. The antibody can also be detectably labelled using fluorescence emitting metals such as $^{152}$Eu, or others of the lanthanide series. These metals can be attached to the antibody using such metal chelating groups such as diethylene-triaminepentaaetic acid (DTPA) or ethylene-diaminetetraacetic acid (EDTA). The antibody also can be detectably labelled by coupling it to a chemiluminescent compound. The presence of the chemiluminescent-tagged antibody is then determined by detecting the presence of luminescence that arises during the course of a chemical reaction. Examples of particularly useful chemiluminescent labelling compounds are luminol, isoluminol, theromatic acridinium ester, imidazole, acridinium salt and oxalate ester. Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labelling are luciferin, luciferase, and aequorin.

To develop all aspects of the present invention, the following studies were performed. Experimental regimens were developed to determine whether critical tumor suppressor phenotypes present in normal oral keratinocytes are lost during oral carcinogenesis. Well-characterized "normal" Type-1 primary cultures and "malignant" HCPC-1 hamster oral keratinocytes (Husain et al. (1989) *Proc. Natl. Acad. Sci.* (*USA*) 86:1264–8; Odukoya et al. (1983) *J. Natl. Can. Inst.* 71:1252–1264; Polverini et al. (1987) *Lab. Invest.* 54:432–41; and Polverini et al (1988) *J. Oral Path.* 17:522–7) cell cultures from the hamster oral cancer model were used to identify suppressed events accumulated during oral carcinogenesis. In vitro phenotypic analyses, such as morphology, growth factor requirements, replicative ability, anchorage dependence, tumorigenicity, and keratin production, have been used to demonstrate the Type I and HCPC-1 hamster oral keratinocytes function similarly to their counterparts in vivo (see, e.g., Husain et al. (1989) *Proc. Natl. Acad. Sci.* (*USA*) 86:1264–8; Odukoya et al. (1983) *J. Natl. Can. Inst.* 71:1252–1264; Polverini et al. (1987) *Lab. Invest.* 54:432–41; and Polverini et al (1988) *J. Oral Path.* 17:522–7).

Complementary DNA (cDNA) libraries were constructed from normal (Type I) and malignant (HCPC-1) cultures of hamster oral keratinocytes. The quality of the isolated mRNA was checked by Northern blot analysis to demonstrate the integrity and satisfactory quality of the housekeeping gene β-actin. Messenger RNA of was used for cDNA library construction. The cDNAs were ligated to BstX1 linkers and then ligated to the phagemid pcDNA II (Invitrogen, San Diego, Calif.). The quality of the two cDNA libraries was determined by the titer, the percent of insert bearing clones, and percent of colonies containing the housekeeping cDNA β-actin. Furthermore, the presence of hamster specific cDNAs was verified by probing for the presence of Syrian hamster specific intracisternal particles H18-IAP (Ono et al. (1985) *J. Virol.* 55:387–394). Using these analyses, it was concluded that the two cDNA libraries to be used as the starting material for subtractive hybridization are representative of genes expressed in normal and malignant hamster oral keratinocytes.

Next, cDNAs that are uniquely or preferentially expressed by normal oral keratinocytes were isolated using subtractive hybridization. Subtractive hybridization has been used successfully to isolate lost transcriptional activity during carcinogenesis. The construction of a subtraction library from normal Type I and malignant HCPC-1 hamster oral keratinocytes allows for the identification of molecular events suppressed during oral carcinogenesis. The method of subtractive hybridization by Klickstein (*Current Protocols in Molecular Biology* (1987) (Austubel et al., eds.) John Wiley & Sons, New York) was used to identify genetic expression that have been lost during hamster oral cancer development. Using 50-fold molar excess of tumor cell (HCPC-1) cDNA, a subtraction library was created with a titer of 384 clones, which were ligated into pBlueScriptII(KS+) phagemid. This subtraction library was screened using differential (+/−) colony hybridization with $^{32}$P-labelled total Type-1 and HCPC-1 cDNA probes. This yielded 130 Type-1 specific clones, ranging in size from 300–1400 bp (average size ~5(X) bp). Individual preparations of these 130 clones and hybridization of these contained cDNA with $^{32}$P-labelled total Type-1 and HCPC-1 cDNA probes revealed that 29 clones are Type-1 specific. Criteria used for further analysis/selection of these 29 clones included: lack of expression in the HCPC-1 cells while detectable expression in Type-1 cells by Northern blot analysis; and evidence of loss of heterozygosity (LOH) by Southern blot analysis. Clones which identified transcriptional activity common to both populations or failed to hybridize to Type-1 mRNA on Northern blots were immediately eliminated. The partial characterization and analysis of one subtraction clone, doc-1, is described below.

When used to label Northern blots containing Type-1 and HCPC-1 mRNA, the hamster doc-1 450 bp cDNA fragment hybridized to am about 1 kilobase (kb) transcript expressed only in the normal Type-1 cells but not in the malignant HCPC-1 cells (FIG. 1A). Furthermore, hybridization of mRNA from three other normal hamster oral keratinocyte cell lines, Type II, Type II/PO, and CL-1, produced detectable hybridization signals but not in another malignant hamster oral keratinocyte cell line, AW16 (FIG. 1B) (Polverini et al. (1988) *Carcinogenesis* 9:117–22; Polverini et al. (1987) *Lab. Invest.* 54:432–41; and Polverini et al (1988) *J. Oral Path.* 17:522–7). In addition, $^{32}$P-labelled doc-1 identified transcripts in mRNA derived from normal hamster tissue in vivo, including submandibular gland, kidney, heart, and lung tissue (FIG. 1C).

These results suggest expression of doc-1 in the hamster is restricted to normal tissue, and its expression is not detectable by Northern blot analysis in malignant hamster oral keratinocytes.

Figure 2:
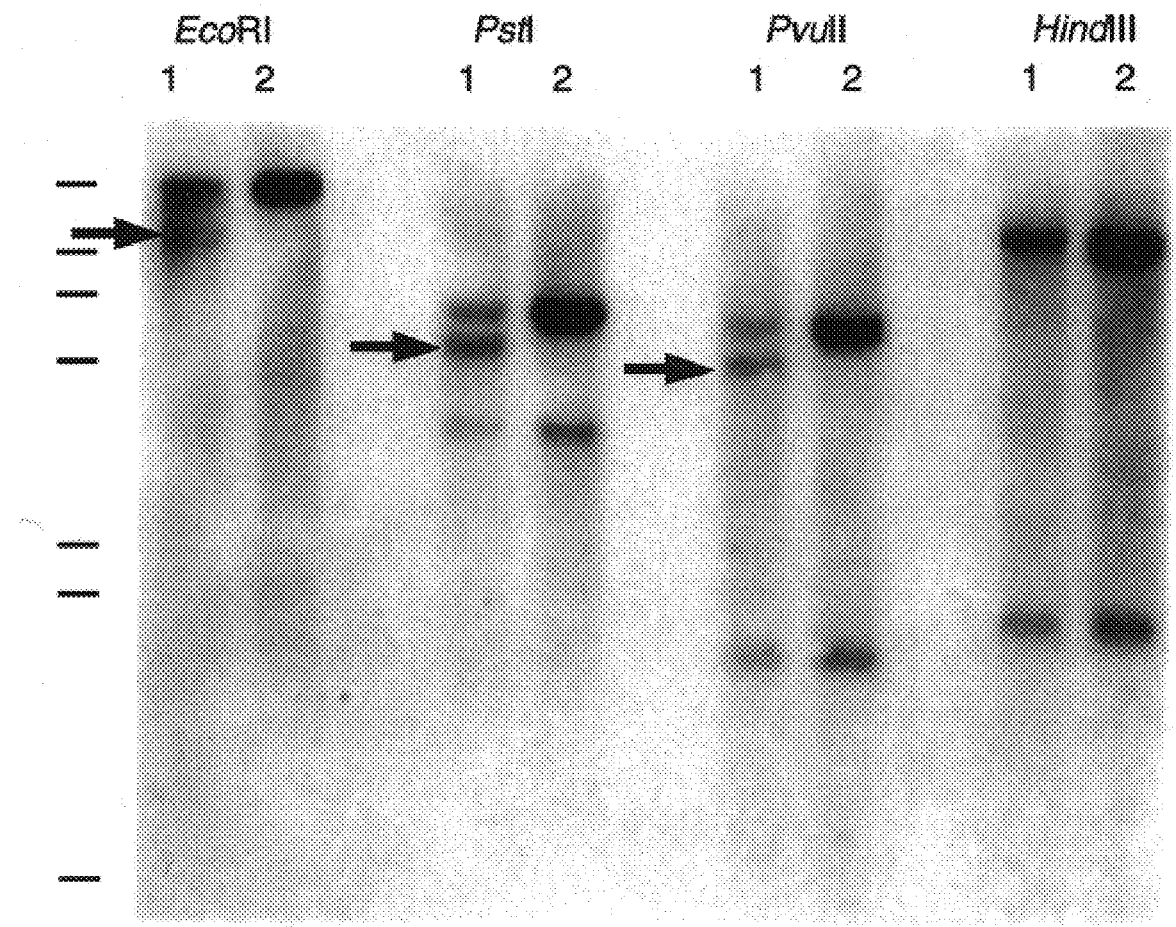
FIG. 2 is a Southern blot showing the genomic organization of the doc-1 locus in normal and malignant hamster oral keratinocytes, wherein genomic DNA from the normal Type I (lanes 1, 3, 5, and 7) and malignant HCPC-1 (lanes 2, 4, 6, and 8) cells was isolated and digested with one of four different restriction endonucleases (Eco RI (lanes 1 and 2), Pst I (lanes 3 and 4), Pvu II (lanes 5 and 6), and Hind III (lanes 7 and 8)) and wherein the arrow indicates lost fragments in three of the four restriction endonuclease digestions of HCPC-1 DNA, and wherein molecular weight markers (Hind III-cut λ DNA) are indicated on the left; 23,130; 9,416; 6,557; 4,361; 2,322; 2,027; and 560 base pairs.

At present, the preponderance of candidate tumor suppressor genes are causally linked by genetic means, through identification of structural alterations of the gene by either somatic or germline mutations (in predisposed humans or animals). FIG. 2 is a Southern blot analysis of Type-1 (lanes 1, 3, 5, and 7) and HCPC-1 (lanes 2, 4, 6, and 8) genomic DNA digested with EcoRI (lanes 1 and 2), PstI (lanes 3 and 4), PvuII (lanes 5 and 6), and HindIII (lanes 7 and 8), hybridized with $^{32}$-P-labelled doc-1 cDNA. In three of the four digestions (EcoRI, PstI, PvuII) there exist a doc-1 hybridizable band (arrow) in Type-1 that is missing in the HCPC-1 cells. A possible interpretation of this is loss of heterozygosity (LOH) or reduction to homozygosity of this locus in the malignant hamster oral keratinocytes. The amount of DNA loaded onto the HCPC-1 lanes is slightly higher that the Type-1 lanes, which resulted in the higher hybridization intensities of the doc-1 bands. This was verified using β-actin rehybridization of these blots.

The original doc-1 cDNA from the subtraction library is a partial cDNA clone, sized at 450-bp. In order to obtain the full-length cDNA, the 3' rapid amplification of cDNA ends (RACE) procedure was initially employed, which yielded a 662-bp poly [A]+ tail containing clone (Frohman et al. (1988) *Proc. Natl. Acad. Sci.* (*USA*) 85:8998–9002). Because the original subtraction and 3' RACE fragments represented ~928 bp of the entire transcript, 5' RACE was employed to obtain a 383 bp clone which yielded the remaining 96-bp of the predicted ~1 kb mRNA. Upon successful cloning and sequencing of the 5' and 3' RACE fragments, new primers were designed to permit re-amplification of the full-length doc-1 cDNA from the Type-1 normal hamster oral keratinocytes. This produced a sequence of 1023-bp (FIG. 3). The sequence shown in FIG. 3 represents the consensus sequence from 10 independent clones, sequenced in both directions.

Open reading frame (ORF) analysis of the full-length doc-1 cDNA revealed that there is an open reading frame of 261-nt extending from nucleotide 91 to 351 which codes for a 87 residue protein with a predicted molecular mass of 9,630 daltons and a p1 of 9.42. The methionine at position 91 is in good context for initiation by Kozak analysis (Kozak (1991) J. Biol. Chem. 266:19867–70). The termination codon at position 351 (TAG) is followed by 646 nt of untranslated sequence ending with a poly(A) tail that is preceded by the consensus polyadenylation signal AATAAA at position 965. In vitro transcription and translation of the full-length doc-1 revealed that the major product is consistent with the predicted open reading frame at 9.6 kDa. A protein data search using the Entrez:Sequence Databases (Release 16.0, National Library of Medicine, Bethesda, Md.) revealed that doc-1 is a novel protein with no significant match. However, using a FASTA program to search for DNA homology of the GenBank (National Library of Medicine, NIH, Bethesda, MD) and EMBL (European Molecular Biology Laboratory Data Library, Cambridge, U.K.) databases revealed that The hamster doc-1 cDNA does exhibit 89% sequence similarity to a 891-bp mouse cDNA sequence (Kopf et al. (1993) Nature (Lond) 326:245–247) which encodes 75 of the 91 amino acids of the open reading frame. This mouse doc-1 homolog gene is inducible in mouse embryo fibroblasts by TNF-α (Gordon et al. (1992) J. Immunol. 148:4021–4027).

If the loss of the transcriptional activity of doc-1 is critical in oral carcinogenesis, then the re-expression of doc-1 in malignant hamster oral keratinocytes should suppress/alter transformed phenotypes. In order to gain insight into the potential tumor suppressor function of doc-1, the full-length cDNA was recloned in-frame into the Kpn1-BamH1 sites of pcDNA3 (pdoc-1), a mammalian expression vector under the control of the cytomegalovirus (CMV) immediate-early promoter (pcDNA3, Invitrogen, San Diego, Calif.). The vector contained the neomycin gene conferring G418 resistance, doc-1 together with pcDNA3 control vectors were transfected into the malignant HCPC-1 hamster oral keratinocytes and stably integrated transfectants were selected in the presence of G418. Fifty-three doc-1 transfectants (HCPC-doc-1) and 10 pcDNA3 control transfectants were selected for further analysis.

Figure 4A:
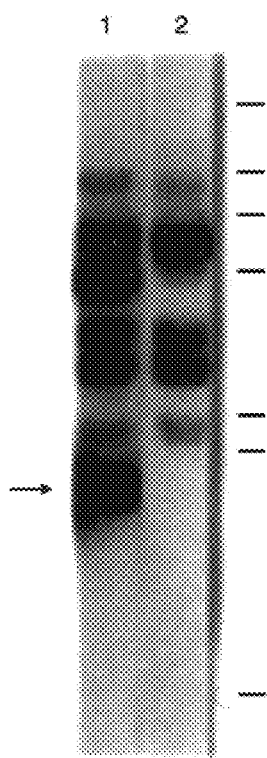
FIG. 4A is a Southern blot showing copy number of transfected doc-1 modules in a representative doc-1 HCPC-1 transfectant clone (lane 1); and in similarly digested DNA from a vector control transfectant (lane 2), wherein intact doc-1 expression module can be identified as an 1,768 bp doc-1 hybridizable fragment (arrow), and wherein molecular weight markers (HindIII-cut λ DNA) are indicated on the left: 23,130; 9,416; 6,557; 4,361; 2,322; 2,027; and 560 base pairs.
Figure 4B:
FIG. 4B is a Northern blot of the same transfectant and control cultures shown in FIG. 4A showing doc-1 transcripts using full-length doc-1 cDNA as a probe, wherein the arrow indicates the doc-1 transcript at about 1 kb, and the markers on the left are 28S and 18S RNA.
Figure 4C:
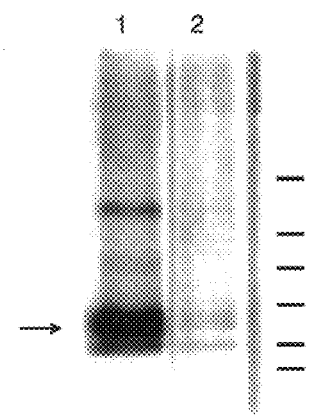
FIG. 4C is a photographic representation of a gel showing immunoprecipitation of the doc-1 protein (predicted to be 9.6 kDa) from the same two transfectants described in FIGS. 4A and 4B, wherein a major product is detected at about 12 kDa (arrow), and the markers on the right are 46, 30, 21.5, 14.3, 6.5, and 3.4/2.35 kDa.

Doc-1 transfectants (HCPC-doc-1) were characterized for the following features. First, intact integration of the expression module (CMV promoter-doc-1) by Southern blotting after double digestion of HCPC-doc-1 genomic DNA by BglII (5' to the CMV promoter) and BamH1 (3' end of doc-1) which should release a 1768-bp fragment. 43 of the 53 (81%) HCPC-doc-1 transfectants demonstrated the presence of the intact expression module (FIG. 4A). Second, the expression of the doc-1 mRNA was detected by Northern blot analysis (FIG. 4B). Using full-length doc-1 cDNA as a probe, a low level of doc-1 transcript is detected in the vector control HCPC-1 transfectants (FIG. 4B). Thirdly, using a polyclonal antibody raised to a synthetic peptide encoding amino acid 70 to 84 in the doc-1 open reading frame, a 12 kDa peptide was detected by immunoprecipitation (FIG. 4C). These results demonstrate that doc-1 can be successfully expressed in the malignant HCPC-1 cells when transformed with doc-1 cDNA. The functional consequences of the transfected doc-1 cDNA expression on the phenotypes of the malignant HCPC-1 cells was evaluated in terms of anchorage dependent growth, cellular morphology, and growth rate.

Figure 5A:
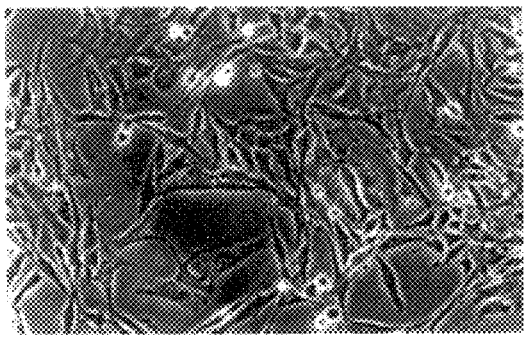
FIG. 5A is a light micrograph of a malignant HCPC-1 culture transfected with the control vector, pcDNA3.
Figure 5B:
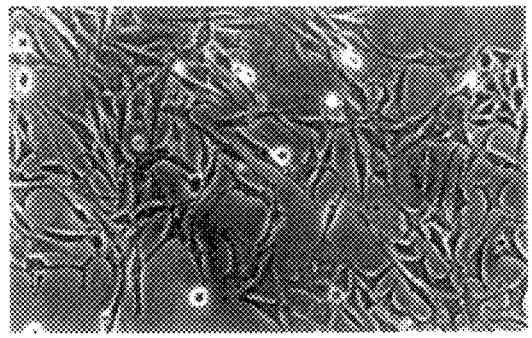
FIG. 5B is a light micrograph of a near confluent culture of a doc-1 HCPC-1 transfectant, clone #28.
Figure 5C:
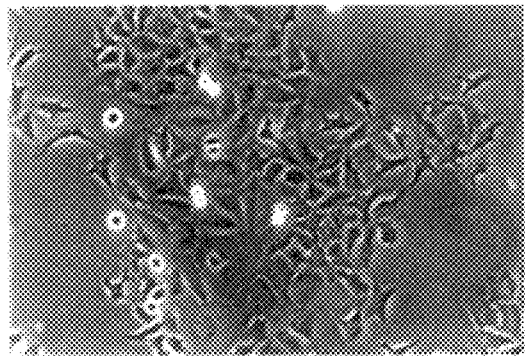
FIG. 5C is a light micrograph of a culture of parental HCPC-1 cells.
Figure 5D:
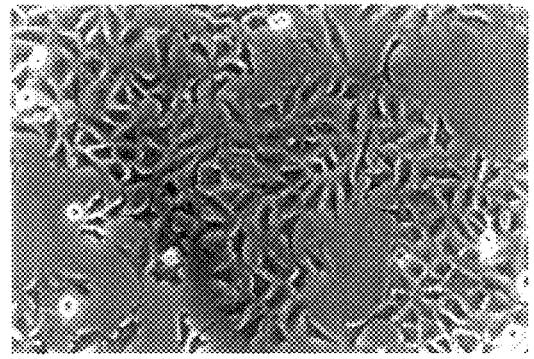
FIG. 5D is a light micrograph of a near confluent culture of the normal Type I hamster oral keratinocyte culture (primary culture)

Compared with HCPC-1 cells transfected with the parental expression vector pcDNA3, 45 of the 53 (85%) of HCPC-doc-1 transfectants demonstrated significantly lesser or no growth in soft agar (p<0.0001). Cellular morphology of HCPC-1 cells transfected with pcDNA3 alone resembled that of the parental cell line: tight packing and polyclonal, as shown in FIGS. 5B and 5D. (Polverini et al. (1986) Lab. Invest. 54:432–41). HCPC-doc-1 transfectants, on the other hand, exhibited a spindly fibroblastoid morphology, resembling that of normal Type-1 hamster oral keratinocytes, as shown in FIGS. 5A and 5C. These cells also exhibit a small nuclear to cytoplasmic ratio, contact inhibition, and a great propensity to terminally differentiate (senesce). In addition, 41 of the 53 clones (82%) of doc-1 transfectants exhibited significantly less colony growth in soft agar (p<0.05) when compared with the vector control transfectants. Table 1 is a summary of the results comparing a representative doc-1 transfectant, clone #28, the vector control (pcDNA3), and the parental HCPC-1 cell line.

TABLE 1

| | doc-1 Transfectant Clone #28 | Vector Control Transfectant pcDNA3 | HCPC-1 (Parental Line) |
|---|---|---|---|
| # Colonies in Soft Agar | 1.0 ± 0.7* | 30.7 ± 2.4 | 33.6 ± 5.4 |
| Doubling Time (Hours) | 13.11 | 9.74 | 10.20 |

*p < 0.0001

Thus, both genetic and functional evidence is provided that doc-1 is a novel tumor suppressor gene that is ubiquitously expressed in normal hamster tissues invivo.

The human form of doc-1 was also partially cloned using PCR and human placental mRNA and primers based on the hamster and mosque doc-1 sequences as the starting material. A 411 base pair product was obtained which is the 3' terminus of the human doc-1 cDNA. This cDNA encodes 21 of the 87 amino acids which are identical between human, mouse, and hamster (IIHARSLBRECLAETERNARS; SEQ ID NO:8). These data suggests that doc-1 is a highly conserved cellular gene.

Figure 8:
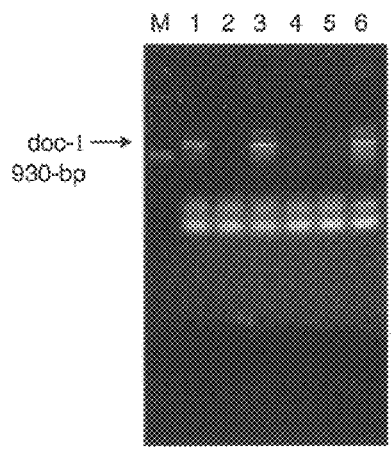
FIG. 8 is a photographic representation of ethidium bromide RT-PCR gel showing the presence of doc-1 mRNA in human malignant oral keratinocytes, wherein human oral cancer cells SCC 15 (lanes 1 and 2), 25 (lanes 3 and 4) and 66 (lanes 5 and 6) were treated with (lanes 1, 3 and 6) and without (lanes 2, 4 and 5) TNF-A.

TNF-α was found to induce doc-1 expression in hamster and human oral keratinocytes. Three human oral (SCC 15, 25, 66) and one cervical (A431) keratinocyte cell lines were phenotyped for TNF-α inducibility of doc-1. Using RT-PCR and human specific TNF-receptor primers (Type I and II), all four cell lines were found to expressed TNF-α Type I and II receptor mRNAs. Incubation of these human oral keratinocytes with TNF-α at 400 U/ml for 4 hours led to the expression of doc-1 mRNA in all four cell lines, as shown in FIG. 8. These results link TNF-α to the expression of doc-1, implicating doc-1 as a downstream mediator in the tumoricidal pathway of TNF-α.

The following examples illustrate the preferred modes of making and practicing the present invention, but are not meant to limit the scope of the invention since alternative methods may be utilized to obtain similar results.

EXAMPLES

1. Cell Culture

The HCPC-1 is a cell line established from a DMBA-induced hamster cheek pouch carcinoma (Odukoya et al. (1983) J. Natl. Can. Inst. 71:1252–1264). AW16, Type II, Type II/PO, and CL-1 cultures are oral keratinocytes isolated from different time points during DMBA-treatment of hamster buccal pouches and were characterized for acquisition of malignant phenotypes by morphology, growth factor requirements, angiogenesis, growth rate, anchorage independent growth, and tumorigenicity (Moroco et al. (1990) *Lab. Invest.* 63:298–306). Type II/PO and CL-1 hamster oral keratinocytes are "normal" established cultures. Type II oral keratinocytes are "partially" transformed hamster oral keratinocyte cultures due to their acquisition of some but not all of the malignant phenotypes. AW16 is another transformed oral keratinocyte cell line derived also from DMBA-treated hamster cheek pouches (Moroco et al. (1990) *Lab. Invest.* 63:298–306). The Type I hamster oral keratinocytes were isolated according to the methods of Solt and co-workers (Polverini et al. (1986) *Lab. Invest.* 54:432–41).

All cell lines and primary cultures were maintained at 37° C., 5% $CO_2$ in DMEM medium supplemented with 10% fetal bovine serum (FBS) (Hazelton, St. Lenexa, Kans.) (except Type I, Type II/PO, CL-1 and AW16 keratinocytes which require 20% FBS) and antibiotics (penicillin (100 units/ml), streptomycin (100 μg/ml), and amphotericin B (0.25 μg/ml) (Whittaker, Mass. Bioproducts, Walkersville, Md.).

2. RNA Isolation and Northern Blotting Total and Poly (A)+ RNA was isolated by CsCl gradient ultracentrifugation guanidine isothiocyanate lysed cells according to the method of Davis et al. (in *Basic Methods in Molecular Biology* (1986) (Davis et al., eds.), Elsevier Science Publishing Co., Inc., New York, pp. 130-136). More specifically, sodium dodecyl sulfate (0.5% SDS) was added into a sterile disposable plastic column packed with autoclaved glass wool and prepared by loading approximately 0.5 ml oligo (dT) cellulose slurry suspended in a loading buffer (20 mM Tris pH 7.4; 0.1 M NaCl; 1 mM EDTA). The column was packed to 0.5 ml, then washed with 3 ml of 0.1 M NaOH with 5 mM EDTA, followed by H2O until the pH was 8, after which a 5 ml wash with loading buffer A (40 mM Tris pH 7.4; 1 M NaCl; 1 mM EDTA; mixed and autoclaved with SDS added to 0.1%) was performed to equilibrate the column. To collect the poly(A)+ RNA, 1.5 ml of elution buffer (10 mM Tris, pH 7.4; 1 mM EDTA mixed and autoclaved with the addition of SDS to 0.05%) was added to the column. One tenth of one volume of 3 M sodium acetate pII 6 along with 2.5 volumes of ethanol were then added. The poly(A)+ RNA was precipitated overnight at −80° C.

Northern blotting was performed using the Zetabind (CUNO, Inc., Meriden, Conn.) membrane as described by Wong et al. (*J. Cell. Biol.* (1985) 101:2245–2252).Exposure time was 14 days at −80° C. Random-priming was used to label the hamster cDNA, as described by Feinberg et al. (*Anal. Biochem.* (1983) 132:6–13).

Figure 1B:
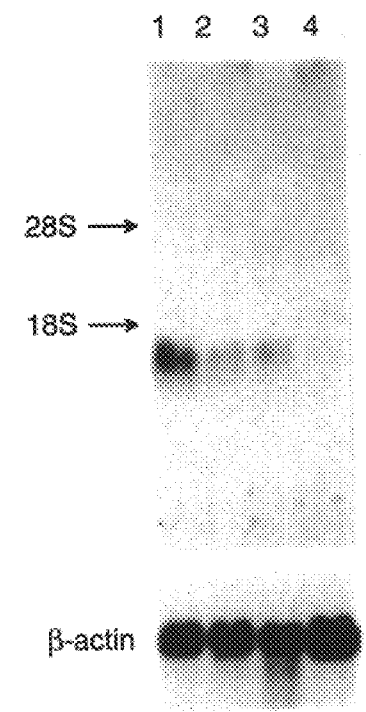
FIG. 1B is a Northern blot showing the presence of doc-1 mRNA in immortalized "normal" hamster oral keratinocyte cell lines, Type II (lane 1), Type II/PO (lane 2), and CL-1 (lane 3), but not in the malignant hamster oral keratinocyte cell line, AW16 (Lane 4)
Figure 1C:
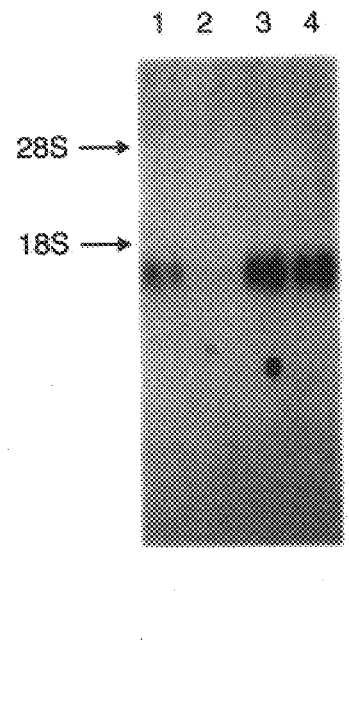
FIG. 1C is a Northern blot showing the presence and absence of doc-1 mRNA in normal hamster submandibular gland, kidney, heart, and lung tissues.

Representative Northern blots are shown in FIGS. 1A–1C. The doc-1 subtraction clone 7.45 was labelled with $^{32}$P-dCTP by the random primer method to a specific activity >1 ×$10^8$ cpm/μg. 0.7×$10^6$ cpm per ml of hybridization solution was used. Northern blots were prepared using 2.0 μg of mRNA from Type I and HCPC-1 keratinocytes. In FIG. 1A, The radiolabelled doc-1 probe identified lost fragments (arrow) in three of the four restriction endonuclease digestions of HCPC-1 DNA, Eco RI digestion of both Type I and HCPC-1 genomic DNA revealed the loss of a 9-kb band in the HCPC-1 DNA. Pst I and Pvu II digestions revealed loss of 5-kb and 4-kb hybridized bands respectively. The appearance of this autoradiograph suggests a deletion has occurred within the gene encoding doc-1.

3. DNA Isolation and Southern Blotting High molecular weight genomic DNA was isolated from the same Type-1 and HCPC-1 cultures used for RNA isolation according to the method of Davis et al. (in *Basic Methods in Molecular Biology* (1986) (Davis et al., eds.), Elsevier Science Publishing Co., Inc., New York, pp. 130–136). Southern blotting was performed using the Zetabind membrane (CUNO, Inc., Meriden, Conn.) as described by Wong et al. (*J. Biol. Chem.* (1984) 259:10738–10744). Random-printing was used to label the hamster cDNA as described by Feinberg et al. (*Anal. Biochem.* (1983) 132:6–13).

FIG. 2 is a representative Southern blot, wherein genomic DNA from the normal Type I (lanes 1, 3, 5, and 7) and malignant HCPC-1 (lanes 2, 4, 6, and 8) cells was isolated and digested with one of four different restriction endonucleases (Eco RI (lanes 1 and 2), Pst I (lanes 3 and 4), Pvu II (lanes 5 and 6), and Hind III (lanes 7 and 8)). The radiolabelled doc-1 probe identified lost fragments (arrow) in three of the four restriction endonuclease digestions of HCPC-1 DNA, Eco RI digestion of both Type I and HCPC-1 genomic DNA revealed the loss of a 9-kb band in the HCPC-1 DNA. Pst I and Pvu II digestions revealed loss of 5-kb and 4-kb hybridized bands respectively. The appearance of this autoradiograph suggests a deletion has occurred within the gene encoding doc-1. Exposure time was 14 days at −80° C. Molecular weight markers (Hind III-cut λ DNA) are indicated on the left; 23,130; 9,416; 6,557; 4,361; 2,322; 2,027; and 560 base pairs;

4. cDNA Library Constructions and Subtractive Hybridization

Messenger RNA was isolated from the Type I (15.7 μg) and HCPC-1 (36.9 μg) hamster keratinocytes as follows. The cultured cells were lysed directly with guanidine isothiocyanate (GIT) buffer. Total RNA was isolated using cesium chloride (CsCl) centrifugation. GIT lysed samples were carefully layered on 5 ml of CsCl buffer and centrifuged in a Beckman SW41 for 21 hours at 32,000 rpm at 20° C. Most supernatant was removed by suction, followed by a sterile Q-tip against the sides of the tube, carefully avoiding disruption of the clear gelatin-like RNA pellet. The pellet was resuspended in 200 ml of a 3 M sodium acetate pH 6 and transferred to a sterile microfuge tube. Residual RNA was resuspended in an additional 200 ml 3 M sodium acetate pII 6 rinse that was also added to the microfuge tube. The addition of 2.5 volumes (1 ml) of ice cold absolute ethanol and vortexing resulted in the precipitation of RNA at −80° C. overnight. After thawing and spinning the sample for 10 minutes at 12,000 rpm, the supernatant was discarded and the pellet dried in a vacuum centrifuge (Speedvac concentrator, SAVANT). The quality of the isolated mRNA was checked by Northern blot analysis to demonstrate the integrity and satisfactory quality of the house-keeping gene β-actin.

The Librarian I cDNA library construction system from Invitrogen (Invitrogen, San Diego, CA) was used to construct the Type I and HCPC-1 cDNA libraries. The quality of the two cDNA libraries was determined by the titer, the percent of insert bearing clones, percent of colonies containing the housekeeping cDNA β-actin. Furthermore, the presence of hamster specific cDNA's was verified by probing for the presence of Syrian hamster specific intracisternal particles H18-IAP, as described by (Ono et al. (1985) *J. Virol.* 55:387–394).

Type I (0.2 μg) and HCPC-1 (10 μg) cDNA inserts were isolated using standard maxiprep procedures (Davis et al. in *Basic Methods in Molecular Biology*, NY, Elsevier Science Publishing Co., Inc, (1986) pp. 130–136) and Apa I/Spe I digestions Sambrook et al. (1989) *Molecular Cloning: A Laboratory Manual*, Cold Spring Harbor Laboratory Press (1989) 5.10–5.11). The size of the insert DNA isolated from each library ranged from about 100 to 2000-bp. The hybridization reaction of the HCPC-1 cDNA with the Type I cDNA fragments was incubated 18 hours at 37° C. The subtracted insert DNA was ligated to prepared phagemid vector pBlue-Script IIKS-(digested wit Spe I and Apa I ends) overnight at 15° C. in a 1:1 insert to plasmid ratio. 384 transformed (white) colonies were isolated.

5. Full-Length Doc-1 cDNA Cloning, DNA Sequence and Predicted Amino Acid Analyses The original doc-1 cDNA from the subtraction library is a partial cDNA clone, sized at 470-bp. In order to obtain clones representing the full-length cDNA, we employed the 5' and 3' RACE (rapid amplification of cDNA ends) procedure (Frohman et al. (1988) *Proc. Natl. Acad. Sci. (USA)* 85:8998–9002). Upon successful cloning and sequencing of the 5' and 3' RACE fragments, new primers were designed to permit re-amplification of the full-length doc-1 cDNA from the Type-1 normal hamster oral keratinocytes.

PCR products were cloned using the CloneAmp System (Gibco-BRL, Gaithersburg, Md.) and subsequently ligated to the vector pAMP 1. Sequencing from 10 independent clones, from both directions, by the dideoxy-chain termination method (Sanger et al. (1977) *Proc. Natl. Acad. Sci. (USA)* 74:5463–5467; and Chiang et al. (1991) *Carcinogenesis* 12:529–532) revealed a 1,023-bp cDNA sequence as shown in FIG. 4.

The resultant nucleic acid and predicted amino acid sequences were analyzed by the MacVector software version 4.1.5 (International Biotechnologies Incorporated, New Haven, Conn.). Searches for related protein sequences were performed using Entrez: Sequences databases from the National Center for Biotechnology Information (Bethesda, Md.). Searches for related DNA sequences was done using a FASTA program to search for DNA homology of the GenBank (National Library of Medicine, NIH, Bethesda, Md.) and EMBL (European Molecular Biology Laboratory Data Library, Cambridge, U.K.) databases. This sequence has been deposited into the NCBI database, and the accession number is U10249.

6. Functional Expression of pdoc-1 Into HCPC-1 Cells In order to express doc-1 in malignant oral tumor cells, the full-length cDNA was recloned inframe into the Kpn1-BamH1 sites of pcDNA3 (pdoc-1), a mammalian expression vector under the control of the cytomegalovirus (CMV) immediate-early promotor (pcDNA3, Invitrogen, San Diego, Calif.). The vector contained the neomycin gene conferring G418 resistance. pdoc-1 together with pcDNA3 control vectors were transfected into the malignant HCPC-1 hamster oral keratinocytes using the Transfectam System (Promega, Madison, Wis.). Stably integrated transfectants were selected in the presence of G418 (400 $\mu$g/ml of DMEM supplemented with 10% fetal bovine serum). Subsequent to selection, all the transfectants were maintained in the presence of 200 $\mu$g/ml of G418.

FIGS. 5A–5D illustrates that the morphology of doc-1 transfectant resembles that of normal hamster oral keratinocytes.

7. Soft Agar and Doubling Time Assays

The transfectants were grown in suspension according to the method of Freshney (Culture of Animal Cells: A Manual of Basic Technique, Wiley-Liss, New York (1994). Cells were seeded at $4\times10^3$ cells in 35 mm dishes in DMEM/1% Agar. Cultures were incubated for 7 days at 37° C. in a $CO_2$ incubator. At the end of the seven days, each dish was stained with a crystal violet solution for overnight at 4° C. Using a dissecting microscope at 25× magnification, 10 fields were randomly chosen and the number of stained colonies counted. The two-tailed Student t-test was used to test the differences between the groups.

For doubling time determination of the transfectants, each of the four transfectant clones were seeded at $2\times10^4$ cells into 24-well plates at 1 ml per well. Quadruplicate wells were used for each of the following time points: 24, 48, 72, 96 and 120 hr. Cells were trypsinized and counted. Results were plotted on a log scale against a linear time scale according to the method of Freshney (*Culture of Animal Cells: A Manual of Basic Technique*, Wiley-Liss, New York (1994). The growth of the cells between days 2 and 3 were used to determine the doubling time according to the following formula for each of the four transfectants: Doubling Time=$[(T_0-T) \log 2]/[\log N-\log N_0]$, where T is the time after inoculation of the cells, and N is the number of cells per $mm^2$.

8. Production of an Antibody Against Hamster Doc-1 Protein and Immunoprecipitation Based on the predicted amino acid sequence of open reading frame (ORF) of doc-1 (nucleotide 10 to 351 encoding 114 amino acids), a polyclonal antibody was produced against a 15 amino acid synthetic peptide corresponding to amino acids 70 to 84 in the doc-1 ORF. This amino acid sequence (SEQ ID NO:5) (EELGKEIRPTYAGSK) was identified to be most antigenic within doc-1 by the method of Jameson et al. (*Comp. Appl. Biosci.* (1988) 4:181–6). The 15 amino acid peptide was synthesized using the Fmoc solid phase methods utilizing MAP resin technology (Tam et al. (1989) *J. Immun. Meth.* 124:53–61). Antibody was generated in two New Zealand white rabbits over 10 weeks using this synthesized peptide. The MAP-peptide was emulsified by mixing with an equal volume of Freund's Adjuvant, and injected into three or four subcutaneous dorsal sites, for total volume of 1.0 ml (0.5 mg of peptide) per immunization. Following the primary immunization, the first and the second boosts were added at weeks 2 and 6. The animals were bled from the auricular artery at weeks 4, 8 and 10. The blood was allowed to clot and serum was collected by centrifugation. The serum was stored at -20° C. Antibody titer was monitored by enzyme linked immunosorbent assay (ELISA) with free doc-1 peptide on the solid phase (1 $\mu$g/well). Serum from the second bleed at 8 weeks yielded the highest titer (400,000 and 500,000 respectively) and was used for the immunoprecipitation studies.

Immunoprecipitation was performed according to the protocol of Harlow et al. (*Antibodies, A Laboratory Manual* (1988) Cold Spring Harbor Laboratory, Cold Spring Harbor, N.Y.). Briefly, 90–95% confluent cultures of transfected cells were starved for overnight with methionine-free, L-glutamine-free D-MEM supplemented with 10% dialyzed fetal bovine serum (Gibco, Grand Island, N.Y.). Doc-1 protein was labelled with 150 $\mu$Ci/ml $^{35}$S-methionine (Amersham, Arlington Heights, Ill.) for 4 hr. Cells were lysed with 1 ml of RIPA buffer with 100 $\mu$g/ml PMSF and 1 $\mu$g/ml aprotinin for 30 min on the ice. Culture dishes were washed with additional 500 $\mu$l of lysis buffer. These cell lysate was centrifuged at 3,200 g for 10 min followed by another centrifugation of the supernatant at 200,000 g for 30 min. The supernatant was then incubated with 50 $\mu$l of rabbit normal serum and 150 $\mu$l of Protein A-agarose for 1 hr. After a five minute centrifugation at 13,000 g, supernatant was transferred into a fresh eppendorf tube and incubated with 60 $\mu$l of rabbit anti-doc-1 pAb (whole serum) for overnight at 4° C. This was followed by an incubation with 150 $\mu$l of Protein A-agarose for 30 min. The doc-1 protein-Protein A-agarose complex was precipitated by centrifugation and washed three times with lysis buffer, then resuspended in 40 $\mu$l of sample loading buffer. After five minutes of boiling, 20 $\mu$l of the denatured sample was loaded into SDS-PAGE Mini Gel system and analyzed by autoradiograph.

FIG. 4C shows representative results. The same two transfectants were assayed for the presence of doc-1 protein by immunoprecipitation using a polyclonal antibody raised against an antigenic domain of the open reading frame (Gimenez-Conti et al. (1993) *Journal of Cellular Biochemistry Supplement*, 83–90). A major product is detected at –12 kDa (arrow). The markers on the right are 46, 30, 21.5, 14.3, 6.5, and 3.4/2.35 kDa. The predicted size of the doc-1 protein is 9.6 kDa.

9. Molecular Cloning of Human Doc-1

The starting material used for the PCR cloning was human placental mRNA (Clontech Cat. No. 64024-1). The primers used were 5' Primer:

```
5'-CATCATTCATGCCCGAAG-3' (Hamster Sequence) (SEQ ID
    NO:6); 3' Primer: 5'-TTGCACTCAACTCCTCGGAG -3'
    (Mouse Sequence)                        (SEQ ID NO:7).
```

These primers were designed based on Hamster and Mouse doc-1 sequences.

10. Expression of Doc-1 in Human Keratinocyte Cell Lines

Figure 9A:
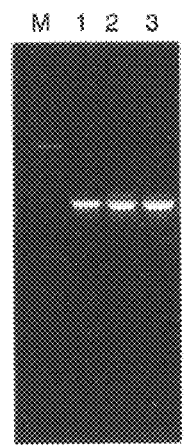
FIG. 9A is a photographic representation of ethidium bromide RT-PCR gel showing the presence of TNF-α receptor Type 1 mRNA in human oral cancer cells SCC 15 (lane 1), SSC 25 (lane 2), and SSC 66 (lane 3)
Figure 9B:
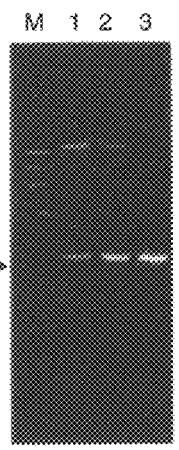
FIG. 9B is a photographic representation of ethidium bromide RT-PCR gel showing the presence of TNF-alpha receptor Type 2 mRNA in human oral cancer cells SCC 15 (lane 1), SSC 25 (lane 2), and SSC 66 (lane 3).

Three human oral keratinocyte cell lines (SCC 15, 25, 66, American Type Culture Collection, Rockville, MD) and one cervical keratinocyte cell line (A431, American Type Culture Collection, Rockville, Md.) were phenotyped for TNF-α inducibility of doc-1 using the reverse transcriptase-polymerase chain reaction procedure (RT-PCR) (Saiki et al. (1988) Science 239:187–191) and human specific TNF-receptor primers Type I and II (Clontech, Palo Alto, Calif.). Cells were treated with and without TNF at 400 u/ml for 4 hours according to the method of Gordon et al. (*J. Immunol.* (1992) 148:4021–4027). All four cell lines were found to expressed TNF-α Type I (FIG. 9A) and II (FIG. 9B) receptor mRNAs. Incubation of these human oral keratinocytes with TNF-α (Genzyme, Cambridge, Mass.) at 400 U/ml for 4 hours led to the expression of doc-1 mRNA in all four cell lines (FIG. 8). Expected size of the doc-1 PCR product is 930-bp. Note that for SCC 66 the loading of the samples of control and TNF-α was reversed from the other 2 cell lines.

11. Expression of Doc-1 in Animal Tissues

Figure 6:
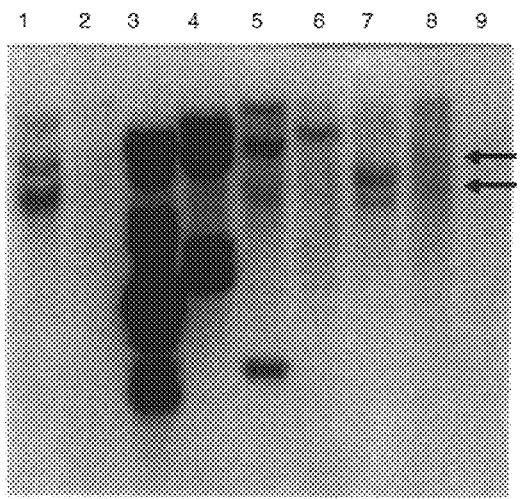
FIG. 6 is a zoo-blot showing the expression of doc-1 in normal EcoRI digested genomic DNA from human (lane 1), monkey (lane 2), rat (lane 3), mouse (lane 4), dog (lane 5), cow (lane 6), rabbit (lane 7), chicken (lane 8), and yeast (lane 9) cells.
Figure 7:
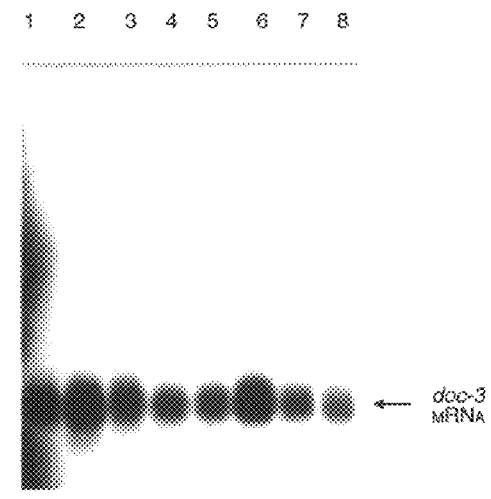
FIG. 7 is a multiple tissue Northern blot showing the presence of doc-1 transcript in normal human heart (lane 2), brain (lane 2), placenta (lane 3), lung (lane 4), liver (lane 5), skeletal muscle (lane 6), and kidney, wherein multiple weight markers are indicated in the left.

Southern blot analysis on human genomic DNA. Using the hamster doc-1 cDNA as a probe to survey a multiple species Zoo blot revealed doc-1 hybridizable sequences in all species examined, including human, supporting the presence of a human homolog. This is shown in FIG. 6.

12. Expression of Doc-1 in Human Tissues

Using the hamster doc-1 cDNA as a probe to survey a human multiple tissue blot containing normal RNA isolated from heart, brain, placenta, lung, liver, skeletal muscle, kidney and pancreas revealed an intense doc-1 transcripts at ~1-kb in all tissues examined. A human normal tissue blot containing mRNA from heart, brain, placenta, lung, liver, skeletal muscle, kidney and pancreas was obtained from Clontech Laboratories Inc. (Palo Alto, Calif.). The nylon membrane was prehybridized with RNA prehybridization mix (5× Denhard's solution, 50 mM sodium phosphate pH 6.5; 50% deionized formamide; 1% glycine; 500 mg/ml denatured salmon sperm DNA; 1% SDS) at 42° C. for at least four hours then hybridized with denatured $^{32}$P-labelled hamster doc-1 cDNA hybridization mix (5× SSC; 1× Denhardts solution; 20 mM sodium phosphate; pH 6.5; 50% deionized formamide; 10% dextran sulfate; 100 mg/ml denatured salmon sperm DNA; and 1% SDS) at 42° C. for 16 hours. The RNA blots were washed with four successive solutions (5×, 2×, 1× SSC, and 1× SSC+0.1% SDS respectively) for 30 minutes in a 42° C. shaking water bath. Following the final wash, the blot was surveyed with a Geiger counter to determine background. All blots were briefly blot dried between 3 mm filter papers, wrapped with Saran wrap, and exposed to Kodak XAR-5 film at –80° C.

Doc-1 expression in head and neck pathologies are also monitored using this procedure. It is expected that cancerous tissues will not express doc-1 in this system.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. An isolated cDNA molecule comprising the nucleotide sequence set forth as SEQ ID NO:3, wherein said cDNA molecule encodes a doc-1 tumor suppressor protein that is inducible by a tumor necrosis factor, and wherein said protein comprises the amino acid sequence set forth as SEQ ID NO:1.

2. An isolated cDNA molecule comprising the nucleotide sequence set forth as SEQ ID NO:4, wherein said cDNA molecule encodes a doc-1 tumor suppressor protein that is inducible by a tumor necrosis factor, and wherein said protein comprises the amino acid sequence set forth as SEQ ID NO:2.

3. A cell transformed with the isolated cDNA molecule of claim 1.

4. The cell of claim 3, wherein the cell is a carcinoma cell.

5. A cell transformed with the isolated cDNA molecule of claim 2.

6. The cell of claim 5, wherein the cell is a carcinoma cell.

* * * * *

SEQUENCE LISTING

```
<160> NUMBER OF SEQ ID NOS: 8

<210> SEQ ID NO 1
<211> LENGTH: 87
<212> TYPE: PRT
<213> ORGANISM: Mesocricetus auratus

<400> SEQUENCE: 1

Met Ala Thr Ser Ser Gln Tyr Arg Gln Leu Leu Ser Asp Tyr Gly Pro
    1               5                   10                  15
    Pro Ser Leu Gly Tyr Thr Gln Gly Thr Gly Asn Ser Gln Val Pro Gln
                20                  25                  30
    Ser Lys Tyr Ala Glu Leu Leu Ala Ile Ile Glu Glu Leu Gly Lys Glu
                35                  40                  45
    Ile Arg Pro Thr Tyr Ala Gly Ser Lys Ser Ala Met Glu Arg Leu Lys
            50                  55                  60
    Arg Gly Ile Ile His Ala Arg Ser Leu Val Arg Glu Cys Leu Ala Glu
    65                  70                  75                  80
    Thr Glu Arg Asn Ala Arg Ser
                    85

<210> SEQ ID NO 2
<211> LENGTH: 21
```

```
<212> TYPE: PRT
<213> ORGANISM: Homo sapiens

<400> SEQUENCE: 2

Ile Ile His Ala Arg Ser Leu Asx Arg Glu Cys Leu Ala Glu Thr Glu
       1               5                   10                  15
      Arg Asn Ala Arg Ser
                  20

<210> SEQ ID NO 3
<211> LENGTH: 1022
<212> TYPE: DNA
<213> ORGANISM: Mesocricetus auratus

<400> SEQUENCE: 3
cccgcgggga tgtcgtacaa gccgaacttg accgcgcaca tgcccgccgc cgccctcaac   60
      gccggaagtg tccactcacc atctactagc atggcgacat cctcccaata tcgccagctg  120
      ctgagtgact acggaccacc gtcactaggc tacacccagg gaactggaaa tagccaagtg  180
      cctcagagta aatatgcaga actgctggcc atcattgaag agttggggaa agagatcaga  240
      cccacttatg cgggaagcaa gagcgccatg gaaagactaa aacgaggcat cattcatgcc  300
      cgaagcctgg ttcgggagtg ctggctgaaa cggaacgtaa tgccaggtcc tagccccctgg  360
      ccagtctgaa ggcccatctt gctacccctt ggagatgaga ggctttgttc aaaatggcag  420
      ttttcctgcc atggtcatta agctctgaac ccacattcaa aagactgaga agacattttg  480
      cagttactga tgatgtgcat tttaagtagt taggaacaat ccaagcattg attttaaaga  540
      tgttttgtgaa gccacttcac agcaagctat tgttttcccc caaataccag tgtcccctta  600
      atctcccttt ggatacattt gccattttgca tcaccccagt tgacttcctt tccaggaggt  660
      cacctgcctc tgaggacctg agtgcaaacc acagcacgtt tgcttagtag ctggcccgcc  720
      tgtgtagacc ctgcttcacg gagcttctct gcttaagtgt ttgcatgact gagtgctttg  780
      aagtcaatct taaaaatgca caagttacag atacagaaga agagcgatct ccaacctacc  840
      aagcgccctg caaatgtcca tcctgagact gtagttctcg gttccatgtt tactgtgaga  900
      tgatcacaac atctggaaga aaatgactga aactgttgca tctttgtatt tattacttga  960
      tgtaataaag cttattttca ttaacagttt gtattaagaa aaaaaaaaa aaaaaaaaaa 1020
      aa                                                                1022

<210> SEQ ID NO 4
<211> LENGTH: 243
<212> TYPE: DNA
<213> ORGANISM: Homo sapiens

<400> SEQUENCE: 4
gctctcccat atggtcgacc tgcaggcggc cgcactagtg attttgcact caactcctcg   60
      gaggcaggtg agctcatgga aaggaagtca actggggtga tgcaaatgga aaatgtatcc  120
      aaagggaggt taaaggggac actggtattt gggacaaac aatagctttt tgtgaagtgg   180
      cttgacaaac atctttcaaa tgcttgaaaa gaaaagagc tgggtcattc ctaactactt  240
      aaa                                                                243

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Glu Glu Leu Gly Lys Glu Ile Arg Pro Thr Tyr Ala Gly Ser Lys
       1               5                   10                  15

<210> SEQ ID NO 6
<211> LENGTH: 18
<212> TYPE: DNA
<213> ORGANISM: Mesocricetus auratus

<400> SEQUENCE: 6
catcattcat gcccgaag                                                 18

<210> SEQ ID NO 7
<211> LENGTH: 20
<212> TYPE: DNA
```

```
<213> ORGANISM: Mus musculus

<400> SEQUENCE: 7
ttgcactcaa ctcctcggag                                        20

<210> SEQ ID NO 8
<211> LENGTH: 21
<212> TYPE: PRT
<213> ORGANISM: Homo sapiens

<400> SEQUENCE: 8

Ile Ile His Ala Arg Ser Leu Asx Arg Glu Cys Leu Ala Glu Thr Glu
        1               5                  10                  15
      Arg Asn Ala Arg Ser
                    20
```